United States Patent
Brumby et al.

(10) Patent No.: US 6,284,779 B1
(45) Date of Patent: Sep. 4, 2001

(54) HETEROAROMATIC COMPOUNDS

(75) Inventors: Thomas Brumby; Fiona McDonald; Eckhard Ottow; Herbert Schneider, all of Berlin (DE)

(73) Assignees: Schering Aktiiengesellschaft, Berlin (DE); Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 09/496,278

(22) Filed: Feb. 1, 2000

Related U.S. Application Data
(60) Provisional application No. 60/126,007, filed on Mar. 24, 1999.

(30) Foreign Application Priority Data

Feb. 3, 1999 (DE) .............................................. 199 05 256

(51) Int. Cl.$^7$ ..................... C07D 413/14; A61K 31/4439

(52) U.S. Cl. .................... 514/340; 546/269.1; 546/269.4

(58) Field of Search ............................. 546/269.1, 269.4; 514/340

(56) References Cited

U.S. PATENT DOCUMENTS

| | | | |
|---|---|---|---|
| 5,455,259 | * 10/1995 | Griffith et al. | 514/357 |
| 5,721,256 | 2/1998 | Jia-He et al. | 514/330 |
| 5,786,378 | 7/1998 | Jia-He et al. | 514/423 |

FOREIGN PATENT DOCUMENTS

| | | |
|---|---|---|
| 0229630 | 7/1987 | (EP) . |
| 9640140 | 12/1996 | (WO) . |
| 9640633 | 12/1996 | (WO) . |
| 9640682 | 12/1996 | (WO) . |
| 9641609 | 12/1996 | (WO) . |
| 9716190 | 5/1997 | (WO) . |
| 976554 | 12/1997 | (WO) . |
| 9822432 | 5/1998 | (WO) . |
| 99/45006 | 2/1999 | (WO) . |
| 9914998 | 4/1999 | (WO) . |
| 9932480 | 7/1999 | (WO) . |
| 9962881 | 12/1999 | (WO) . |
| 9965451 | 12/1999 | (WO) . |
| 0016603 | 3/2000 | (WO) . |

OTHER PUBLICATIONS

Matsumura, Y. et al., "New Synthetic Method of Optically Active alpha–Methylproline and alpha–Methylpipecolinic Acid using Electrochemical Oxidation as a Key Reaction," *Tetrahedron Letters*, NL, Elsevier Science Publishers, Amsterdam, vol. 37, No. 46, pp. 8395–8398 (Nov. 11, 1996).
Asen H. Koedjikov et al., "The gem–dimethyl effect on reactivities in cyclizations through tetrahedral intermediates," *Journal of the Chemical Society*, Perkin Transactions 2, pp. 2479–2487 (1996).

Chat–On Chan et al., "Preparation, isolation and X–ray crystallographic structure determination of a stable, crystalline carbonic anhydride of an N–protected alpha–amino acid," *Journal of the Chemical Society*, Perkin Transactions 1, pp. 777–779 (1992).
I. B. Blagoeva et al., "Change of rate determining step induced by the gem–dimethyl effect," *Journal of the Chemical Society*, Perkin Transactions 1, pp. 1157–1158 (1989).
Ergun Atay et al., "On the disappearance of the gem–dimethyl effect," *Journal of the Chemical Society*, Perkin Transactions 2,, pp. 2289–2297 (1998).
Takeo Kawabata et al., "Direct asymmetric alpha–alkylation of phenylalanine derivatives using no external chiral sources," *Journal of the American Chemical Society*, vol. 116, No. 23, pp. 10809–10810 (1994).
Arwel Lewis et al, "Design, construction and properties of peptide N–terminal cap templates ddevised to initiate alpha–helices," *Journal of the Chemical Society*, Perkin Transactions 1, pp. 3777–3793 (1998).
Chemical Abstracts, vol. 130, No. 2 (Jan. 11, 1999)—Abstract No. 14232s, Thieriet, N. et al., "Tandem deprotection–coupling . . . ," p. 470, col. 1—XP002140321 abstract & Pept. 1996, Proc. Eur. Pept. Symp., pp. 823–824 (1998).
Fujisawa, Tamotsu et al, "Sterocontrolled addition reaction of organometallics to chira.alpha.–keto amides," *Bull. Chem. Soc. Jpn.*, 63(7), pp. 1894–1897 (1990).
Koft, Emil R. et al., "The formation and alkylation of alpha.–keto amide dianions," *Tetrahedron Lett.*, 27(20), pp. 2227–2230 (1986).
Byun, II Suk et al., "Highly diastereoselective reduction of new chiral alpha–keto amides," *Synth. Commun.*, 25(13), pp. 1963–1969 (1995).
Okamoto, Yoshio et al., "Asymmetric polymerization of aromatic isocyanates with optically active anionic initiators," *J. Polym. Sci., Part A: Polym. Chem.*, 32(2), pp. 309–315 (1994).
Tsuge H. et al., "Highly Diastereoselective MichaelAddition to Optically Active Trifluoromethylated alpha, beta–unsaturated Sulfonamides Based on their Hinge–Like Conformation," *Tetrahedron*, NL, Elsevier Science Publishers, Amsterdam, vol. 53, No. 3, pp. 823–838 (Jan. 20, 1997).

(List continued on next page.)

*Primary Examiner*—Jane Fan
(74) *Attorney, Agent, or Firm*—Millen, White, Zelano & Branigan, P.C.

(57) ABSTRACT

The invention relates to the compounds of Formula I

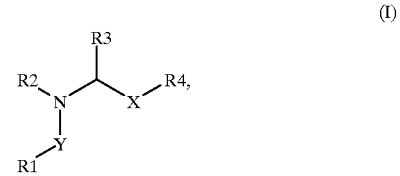

(I)

as well as the process for their production and their use as pharmaceutical agents.

20 Claims, No Drawings

OTHER PUBLICATIONS

Ibuka, Toshiro et al., "Aza–Payne Rearrangement of Activated 2–Aziridinemethanols and 2,3–Epoxy Amines under Basic Conditions," *J. Org. Chem.*, 60(7), pp. 2044–2058 (1995).

Choji, Kashima et al., "Lithium Aluminium Hydride Reduction of Chiral Benzoylformamides Derived from Chiral Amino Alcohols," *J. Chem. Perkins Trans. 1*, pp. 1495–1500 (1987).

Van Den Broek, Leon A.G.M. et al., "Asymmetric Diels–Aider reactions with sulfines derived from proline," *J. Org. Chem.*, 49(10), pp. 1691–1695 (1994).

Nkunya, M.H.H. et al., "Asymmetric synthesis of alpha., beta epoxy sulfonamides (oxiranesulfonamides)," *Recl. Trav. Chim. Pays–Bas*, 104(10), pp. 253–259 (1985).

Thomas, R.M. et al., "An efficient and selective deprotection of allyl ethes by a Cecl3.7H20– NaI system," *Tetrahedron Letters*, NL, Elsevier Science Publishers, Amsterdam, vol. 40, No. 40, pp. 7293–7294 (Oct. 1, 1999).

Harvill, E. K., et al., "Haloalkyltetrazole and aminoalkyltetrazole derivatives," *Journal of Organic Chemistry*, vol. 17, No. 12, pp. 1597–1616 (Dec. 1952).

Dondoni, A. et al., "Addition of 2–silylazoles to heteraryl cations. Synthesis of unsymmetrical azadiaryls," *Tetrahedron Letters*, vol. 25, No. 33, pp. 3637–3640 (1984).

Shono, T. et al., "A new synthetic method of 1–azabicyclo '4.n.0 systems," *Chemistry Letters*, No. 1, pp. 21–24 (Jan. 1983).

Garvey, D. S. et al., "Ligands for brain cholinergic channel receptors: Synthesis and in vitro characterization of novel isoxazoles and isothiazoles as bioisosteric replacements for the pyridine ring in nicotine," *Journal of Medicinal Chemistry*, vol. 37, No. 26, pp. 4455–4463 (Dec. 23, 1994).

Falorni, M. et al., "Synthesis of chiral pyrazoles and isoxazoles as constrained amino acids," *Tetrahedron: Asymmetry*, vol. 9, No. 17, pp. 3039–3046 (Sep. 4, 1998).

Kiyooka, S. I. et al., "A short synthesis of a Pyrrole Derivative Having a Chiral Substituent," *Synthesis*, vol. 9, pp. 745–746 (Sep. 1, 1988).

Hamilton, G. S., "Immunophilin Ligands for the Treatment of Neurological Disorders," *Expert Opinion on Therapeutic Patents*, vol. 8, No. 9, pp. 1109–1124 (1998).

CA 109:210794, Murata et al., 1988.*

CA 126:144545, Hamilton et al., 1988.*

* cited by examiner

HETEROAROMATIC COMPOUNDS

This application claims the benefit of the filing date of U.S. Provisional Application Ser. No. 60/126,007 filed Mar. 24, 1999.

The invention relates to heteroaromatic compounds, the process for their production and their use in pharmaceutical agents.

It has been reported that compounds with an affinity for the FK506 binding protein (FKBP) that inhibit that protein's rotamase activity also possess nerve growth stimulatory activity. [Lyons et al., *PNAS,* 91, pp. 3191–3195 (1994)]. Many of these such compounds also have immunosuppressive activity.

FK506 (Tacrolimus), an immunosuppressive drug, has been demonstrated to act synergistically with NGF in stimulating neurite outgrowth in $PC_{12}$ cells as well as sensory ganglia [Lyons et al. (1994)]. This compound has also been shown to be neuroprotective in focal cerebral ischemia [J. Sharkey and S. P. Butcher, *Nature,* 371, pp. 336–339 (1994)] and to increase the rate of axonal regeneration in injured sciatic nerve [B. Gold et al., *J. Neurosci.,* 15, pp. 7509–16 (1995)].

The use of immunosuppressive compounds, however, has obvious drawbacks. In addition to compromising immune function, prolonged treatment with these compounds can cause nephrotoxicity [Kopp et al., *J. Am. Soc. Nephrol.,* 1, p. 162 (1991)], neurological deficits [P. C. DeGroen et al., *N. Eng. J. Med.,* 317, p. 861 (1987)] and vascular hypertension [Kahan et al., *N. Eng. J. Med.,* 321, p. 1725 (1989)].

More recently, sub-classes of FKBP binding compounds which inhibit rotamase activity, but which purportedly lack immunosuppressive activity have been disclosed for use in stimulating nerve growth [see U.S. Pat. Nos. 5,614,547; 5,696,135; WO 96/40633; WO 96/40140; WO 97/16190; J. P. Steiner et al., *Proc. Natl. Acad. Sci. USA,* 94, pp. 2019–23 (1997); and G. S. Hamilton et al., *Bioorg. Med. Chem. Lett.,* 7, pp. 1785–90 (1997)]. While these compounds supposedly avoid certain unwanted side effects of immunosuppressive FKBP binding compounds, they still bind to FKBP and inhibit its rotamase activity. This latter property may still lead to undesirable side effects due to other roles FKBP may play in mammals.

Surprisingly, it is now known that binding to FKBP is not necessary for neuronal activity. Co-pending U.S. patent application Ser. Nos. 08/748,447, 08/748,448 and 08/749,114, each of which is incorporated by reference in its entirety, each describe the use of non-FKBP binding, non-immunosuppressive compounds for stimulating nerve growth and preventing neurodegeneration. Due to their lack of affinity for FKBP, these compounds advantageously avoid any potential interference with FKBP-associated biochemical pathways. These compounds do, however, inhibit multi-drug resistance ("MDR") through inhibition of the p-glycoprotein and MRP. While it appears that the dosages of those compounds necessary to stimulate nerve growth and prevent neurodegeneration are lower than those that effect MDR, it would still be desirable to obtain compounds which are specific for neuronal activity, without other significant mechanisms of action.

It is known that piperidine and pyrrolidine derivatives have immunosuppressive and non-immunosuppressive properties. For example, WO 96/40633 describes that N-glyoxyl-prolylester compounds, which have an affinity to FKBP receptors, have a neurotrophic action and stimulate neuronal regeneration as inhibitors of the FKBP-rotamase.

The stimulation of neurite growth in nerve cells with piperidine derivatives is described in WO 96/41609, which is incorporated by reference herein in its entirety. The clinical use of the previously known piperidine and pyrrolidine derivatives for stimulation of neurite growth does not increase the chances of success, since the compounds are unstable in plasma and do not pass through the blood-brain barriers in sufficient amounts. WO 99/10340 also discloses compounds having neuronal activity. Its entire disclosure is also incorporated by reference herein.

Applicants have identified several subclasses of compounds that have potent neuronal activity.

The term "neuronal activity," as used herein, includes stimulation of damaged neurons, promotion of neuronal regeneration, prevention of neurodegeneration and treatment of a neurological disorder. The compounds of this invention have activity in both peripheral nerves and the central nervous system.

Applicants have discovered diverse genera of compound with neuronal activity which do not bind to FKBP, and which do not have multi-drug resistance reversal activity. Without being bound by theory, applicants believe that the compounds disclosed in this application exert their neuronal activity by increasing cytoplasmic $Ca^{2+}$ concentrations. This is likely achieved by interaction, either direct or indirect, with a calcium release channel, such as the ryanodine receptor or the inositol 1,4,5-trisphosphate receptor, in the endoplasmic reticulum of the nerve cell.

Thus, according to one embodiment, the invention provides a method of stimulating nerve growth or preventing neurodegeneration by contacting nerve cells with a compound that:

a. increases cytoplasmic $Ca^{2+}$ concentration or binds to the ryanodine receptor;

b. does not bind to FKBP; and c. does not possess MDR reversal activity.

According to a related embodiment, the present invention provides a compounds that:

a. has neuronal activity;

b. increases cytoplasmic $Ca^{2+}$ concentration or bind to the ryanodine receptor;

c. does not bind to FKBP; and d. does not possess MDR reversal activity.

The term "increases cytoplasmic $Ca^{2+}$ concentration," as used herein means a detectable increase in channel current recorded in the single channel recording assay described below in the presence of such a compound as compared to an appropriate control. Alternatively, the term "increases cytoplasmic $Ca^{2+}$ concentration," as used herein means a detectable shift in the fluorescence spectrum in the cell assay described herein.

The term "binds to the ryanodine receptor," as used herein, means that the compound specifically competes with ryanodine for binding to microsomes in the assay described below.

The term "does not bind FKBP," as used herein means that the compound demonstrates a Ki of 10 $\mu$M or greater in at least one of the rotamase inhibitory assays described below.

The term "does not possess MDR reversal activity," as used herein means that at a concentration of 2.5 $\mu$M, the compound has an MDR ratio of less than 7.0, and preferably less than 3.0 in at least one of the MDR assays described below.

Single-channel recording experiments are useful to determine if the compounds of this invention cause the requisite increase in cytoplasmic Ca$^{2+}$ concentration. These experiments are conducted as described in E. Kaftan et al., *Circulation Research*, 78, pp. 990–997 (1996), the disclosure of which is herein incorporated by reference. Single channel recordings are conducted under voltage clamp conditions with a pair of Ag/AgCl electrodes contacting the solutions via CsCl junctions. Vesicles are added to the cis chamber and fused with planar lipid bilayers composed of phosphatidylethanolamine/phosphatidylcholine (3:1, 30 mg/ml in decane, Avanti Polar Lipids). The trans chamber contains 250 mM HEPES and 53 mM B(OH)$_2$, pH 7.35; the cis chamber contains 250 mM HEPES-Tris pH 7.35. Compounds dissolved in methanol are added to the cis chamber. Channel currents are amplified using a bilayer clamp amplifier (BC-525A, Warner Instruments) and recorded on VHS tape (Dagen Corp.). Data are filtered to an eight-pole Bessel filter (Frequency Devices) to 500 Hz, digitized at 2 kHz, transferred to a personal computer, and analyzed with pclamp version 6.0 (Axon Instruments). Single channel recordings are done at least 3 times for each compound condition.

Ryanodine binding may be measured by incubating microsomal protein with $^3$H-ryanodine in buffer containing 36 mM Tris pH 7.2 and 50 mM KC$_1$ in the absence or presence of test compounds. Controls for maximum binding were done in the presence of 0.72 mM ATP and 36 μM CaCl$_2$. Nonspecific binding was measured in the presence of 25 μM unlabeled ryanodine. Binding reactions were incubated for 2 hours at room temperature, and then centrifuged for 15 minutes at 30,000×g. The pellets were solubilized and the radioactivity was measured by scintillation counting.

Alternatively, the flux of cytoplasmic Ca$^{2+}$ into the cell can be followed fluorescently. For example, neuronal cells can be incubated with NGF and a calcium binding fluorescent dye, such as Fura-2, in a calcium-containing buffer. Cells are imaged continuously both before and after the addition of a test compound of this invention. The difference in fluorescent intensity before and after the addition of compounds is then plotted as a ratio of fluorescence units at 340 nm and 380 nm.

Testing a compound of this invention to confirm that it binds to FKBP12 with a Ki of 10 μM or higher may be achieved using several assays known in the art. In particular, those compounds may be assayed for their ability (or lack thereof) to inhibit rotamase. Examples of assays that measure inhibition of FKBP12 rotamase activity are those in which the isomerization of an artificial substrate—N-succinyl-Ala-Ala-Pro-Phe-p-nitroanilide— is followed spectrophotometrically [M. W. Harding et al., *Nature*, 341, pp. 758–60 (1989); by J. J. Siekierka et al., *Nature*, 341, pp. 755–57 (1989); and S. T. Park et al., *J. Biol. Chem.*, 267, pp. 3316–24 (1992)]. The assay includes the cis form of the substrate, FKBP12, the compound to be tested and chymotrypsin. Chymotrypsin is able to cleave p-nitroanilide from the trans form of the substrate, but not the cis form. Release of p-nitronilide is measured.

Other FKBP binding assays include a competitive LH20 binding assay using labeled FK-506 as a reporting ligand. These have been described by M. W. Harding et al., *Nature*, 341, pp. 758–60 (1989) and by J. J. Siekierka et al., *Nature*, 341, pp. 755–57 (1989).

To determine whether a compound according to this invention has the requisite MDR ratio below 7.0, any of the assays described in U.S. Pat. Nos. 5,543,423, 5,717,092, 5,726,184 or 5,744,485, the disclosures of which are herein incorporated by reference in their entireties, may be utilized.

In particular, cell lines which are known to be resistant to particular drug are employed. These cell lines include, but are not limited to, the L1210, P388D, HL60 and MCF7 cell lines. Alternatively, resistant cell lines may be developed. The cell line is exposed to the drug to which it is resistant, or to the test compound; cell viability is then measured and compared to the viability of cells which are exposed to the drug in the presence of the test compound ("MDR ratio")

The compounds of Formula I are metabolically stable and pass through the blood-brain barriers and stimulate the neurite growth by itself or in combination with neuronal growth factors. Since the new compounds also do not show any significant side effects, they are suitable for treatment of the various neuropathological diseases, which are affected by neuronal regeneration and growth, such as, e.g., peripheral nervous disturbances, which are caused by physical injuries or diseases such as diabetes; physical injuries of the central nervous system (e.g., of the brain or spinal cord); strokes; neurological disorders by neurodegenerations such as Parkinson's disease, Alzheimer's disease and amyotrophic lateral sclerosis.

The invention relates to the compounds of Formula I and their physiologically compatible salts

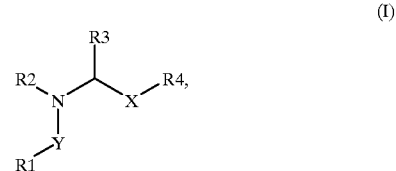

in which

R$^1$ is hydrogen, Ar, straight-chain or branched C$_1$–C$_7$ alkyl, which can be substituted with Ar or E, straight-chain or branched C$_2$–C$_7$ alkenyl, which can be substituted with Ar or E, C$_3$–C$_7$ cycloalkyl, which can be substituted with Ar or E or C$_5$–C$_7$ cycloalkenyl, which can be substituted with Ar or E, Y is —(C=O)—(C=O)—, O)—, O$_2$—, —(C=O)NH—, —(C=S)NH—, —(C=O)—(C=O)—O—, —(C=O)—(C=O)NH—, —(C=O)—O— or O)—, O—NH—, R$^2$ is straight-chain or branched C$_1$–C$_6$ alkyl, which can be substituted with phenyl or halogenated phenyl, R$^3$ is straight-chain or branched C$_1$–C$_6$ alkyl, straight-chain or branched C$_2$–C$_6$ alkenyl, C$_3$–C$_7$ cycloalkyl, C$_5$–C$_7$ cycloalkenyl, cyclohexylmethyl, whereby the alkyl, alkenyl, cycloalkyl and cycloalkenyl radical can be substituted by the same or a different Ar group in one to two places, or R$^2$ and R$^3$ together with the N-atom form a 5- to 7-membered heterocycle, which can be saturated or unsaturated and which can be substituted with C$_1$–C$_4$ alkyl and OH, X is a 5-membered heteroaryl with 1–3 N, O or S atoms, R$^4$ means Ar, straight-chain or branched C$_1$–C$_9$ alkyl, straight-chain or branched C$_2$–C$_9$ alkenyl, C$_3$–C$_7$ cycloalkyl, C$_5$–C$_7$ cycloalkenyl, whereby the alkyl radical and the alkenyl radical can be substituted with Ar, C$_3$–C$_7$ cycloalkyl and C$_5$–C$_7$ cycloalkenyl by the same or different groups in one to two places, and Ar is a C$_6$–C$_{12}$ mono- or bicyclic aromatic compound, which can contain 0 to 4 N, S or O atoms and which optionally is partially hydrogenated and which can be substituted with E in one to three places, and E is halogen, hydroxy, nitro, CF$_3$, CN, OCF$_3$, amino, phenyl, methylenedioxy, phenoxy, benzyloxy, C$_1$–C$_4$ alkoxy or C$_1$–C$_4$ alkyl.

The compounds of Formula I can also be present as stereoisomers, geometric isomers or stable tautomers. The invention comprises all possible isomers, such as E- and Z-isomers, S- and R-enantiomers, diastereomers, racemates and mixtures thereof. The stereochemistry of the CH group, which carries substituents $R^3$, can be R or in particular S. Conventional methods can be used to prepare the desired structures, e.g., enzymatic, (chiral) HPLC, diastereomer formation, etc.

The physiologically compatible salts can be formed with inorganic and organic acids, such as, for example, oxalic acid, lactic acid, citric acid, fumaric acid, acetic acid, maleic acid, tartaric acid, phosphoric acid, HCl, HBr, sulfuric acid, p-toluenesulfonic acid, methanesulfonic acid, i.a.

In each case, alkyl means a straight-chain or branched alkyl group, such as, e.g., methyl, ethyl, propyl, isopropyl, n-butyl, sec-butyl, tert-butyl, n-pentyl, sec-pentyl, tert-pentyl, neopentyl, n-hexyl, sec-hexyl, heptyl, octyl, nonyl.

The alkenyl substituents contain at least one double bond, such as, for example, the following radicals: vinyl, 2-propenyl, 1-propenyl, 2-butenyl, 1-butenyl, 1-methyl-1-propenyl, 2-methyl-2-propenyl, 3-methyl-2-propenyl, 1-penten-3-yl, n-hexenyl, 1-hepten-4-yl.

Cycloalkyl is defined in each case as cyclopropyl, cyclobutyl, cyclopentyl, cyclohexyl and cycloheptyl.

Cycloalkenyl means, e.g., cyclopentenyl, cyclohexenyl and cycloheptenyl.

In each case, halogen means fluorine, chlorine, bromine or iodine.

As a 5-membered heteroaryl radical X, there can be mentioned, for example: 1,2,4-oxadiazolyl, 1,3,4-oxadiazolyl, thiazolyl, oxazolyl, thienyl, isoxazolyl, preferably 1,2,4-oxadiazol-5-yl, which is substituted in 3-position with $R^4$.

In each case, in the embodiment that does not contain heteroatoms, Ar is defined as 1- and 2-naphthyl, biphenyl, indenyl and preferably phenyl.

In the embodiment that contains heteroatoms, Ar is a monocyclic or bicyclic heteroaromatic compound, which contains 5 to 6 ring members in each ring and 1 to 4 heteroatoms and which can be partially hydrogenated; Ar preferably means a 5- or 6-ring that contains 1 to 3 heteroatoms and that can have a benzene ring fused, whereby the bonding in general is via carbon atoms.

For example, the following heteroaromatic compounds can be mentioned: furyl, thienyl, pyridyl, pyrrolyl, oxazolyl, thiazolyl, isothiazolyl, imidazolyl, pyrazolyl, isoxazolyl, triazolyl, oxadiazolyl, pyrimidinyl, pyrazinyl, indolyl, benzimidazolyl, benzothiophenyl, quinolinyl, isoquinolinyl, quinoxalinyl, 1,2,3,4-tetrahydroquinolinyl and benzothiazolyl. Preferred are pyridinyl, thienyl, furyl, thiazolyl, indolyl, quinolinyl, and isoquinolinyl. Especially preferred are 2-, 3- and 4-pyridyl, 2- and 3-thienyl, 2- and 3-indolyl, and 2-, 4- and 5-thiazolyl, and especially pyridyl.

The invention also relates to the compounds of Formula IA, their isomers and physiologically compatible salts

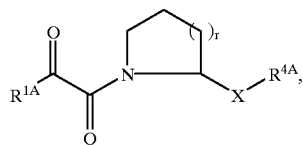

(IA)

in which
$R^{1A}$ is straight-chain or branched $C_1$–$C_7$ alkyl, straight-chain or branched $C_2$–$C_7$ alkenyl, $C_3$–$C_5$ cycloalkyl, $C_5$–$C_7$ cycloalkenyl or Ar' optionally substituted with halogen, hydroxy, nitro, $CF_3$, $C_1$–$C_4$ alkoxy or $C_1$–$C_4$ alkyl, X is a 5-membered heteroaryl with 1–3 N, O or S atoms, $R^{4A}$ is straight-chain or branched $C_1$–$C_7$ alkyl, straight-chain or branched $C_2$–$C_7$ alkenyl, $C_{3-5}$ cycloalkyl, $C_5$–$C_7$ cycloalkenyl, whereby the alkyl radical and the alkenyl radical can be substituted by the same or a different Ar' group in one to two places, r is 1 or 2, and Ar' means $C_6$–$C_{12}$ aryl or 5- or 6-membered heteroaryl with 1–3 N, O or S atoms, whereby the aryl radical and the heteroaryl radical can be substituted with halogen, hydroxy, $C_1$–$C_4$ alkoxy, nitro, $CF_3$ or $Cl$-$C_4$ alkyl by the same or a different group in one to three places.

Preferred embodiments of $R^1$ are Ar, straight-chain or branched $C_1$–$C_7$ alkyl, which can be substituted with Ar or E, and $C_3$–$C_7$ cycloalkyl, which can be substituted with Ar or E, whereby in the case of cycloalkyl, E means in particular $C_1$–$C_4$ alkyl. Especially preferred are phenyl optionally substituted with E and straight-chain or branched $C_1$–$C_7$ alkyl optionally substituted with E. In particular, $C_{3-7}$ alkyl and 3,4,5-trimethoxyphenyl can be mentioned.

Preferred embodiments of Y are —$SO_2$—, —(C=O)NH—, —(C=S)NH—, —$SO_2$—NH— and especially —(C=O)—(C=O)—.

A preferred embodiment of $R^2$ is methyl, ethyl and benzyl optionally substituted with halogen in one to three places in an aromatic compound.

A preferred embodiment of $R^3$ is straight-chain or branched $C_1$–$C_6$ alkyl, which can be substituted with Ar in one to two places, whereby Ar can be substituted with E in one to three places.

If $R^2$ and $R^3$ together with the nitrogen atom form a heterocycle, the latter preferably has 5 to 7 ring members and is saturated; pyrrolidine and piperidine are especially preferred. As preferred embodiments of $R^2$ and $R^3$, $R^2$ and $R^3$ together with the nitrogen atom form a saturated heterocycle with 5 to 6-ring members, such as pyrrolidine and piperidine.

In each case, E preferably means halogen, hydroxy, nitro, is $CF_3$, CN, $C$—$C_4$ alkoxy and $C_1$–$C_4$ alkyl.

Preferred embodiments of $R^4$ are straight-chain or branched $C_1$–$C_9$ alkyl, which optionally is substituted with Ar in up to four places or Ar optionally substituted with E.

$R^4$ is especially preferably in the meaning of a straight-chain or branched $C_1$–$C_7$ alkyl radical, which is substituted with Ar in one to two places in terminal position.

$R^4$ can be mentioned with the structure

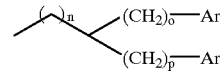

in which Ar has the above-mentioned meaning, and o and p mean 0, 1, 2 or 3, and n is 0 or 1.

The embodiments of the compounds of Formula I that are mentioned above as preferred are also preferred embodiments of the compounds of Formula IA.

The invention also relates to the use of the compounds of Formula I for the production of a pharmaceutical agent for stimulation of neuronal activity. The compounds of Formula I are suitable for stimulation of neurite growth in nerve cells, for stimulation of neuronal regeneration, for prevention of neurodegeneration, for treatment of neurological diseases such as neurodegeneration and for treatment of peripheral neuropathies. The prevention and treatment of neuron cell death, which is triggered by a variety of diseases or physical trauma, is therefore made possible with the compounds of Formula I. The methods of stimulating nerve growth and preventing neurodegeneration disclosed herein employ the above compounds either alone or in combination with a neuronal growth factor. The methods are useful in treating or preventing nerve damage caused by various neurological diseases and physical traumas and also in ex vivo nerve regeneration.

Diseases that according to the invention can be treated or prevented with the compounds of Formula I are in particular trigeminal neuralgia, glossopharyngeal neuralgia, Bell's palsy, myasthenia gravis, muscular dystrophy, muscular trauma, progressive muscular atrophy, peripheral neuropathies, peripheral myelin disorders, Alzheimer's disease, Guillain-Barré syndrome, Parkinson's disease, amyotrophic lateral sclerosis, Tourette's syndrome, multiple sclerosis, central myelin disorders, strokes, ischemia, neural degenerative diseases, trauma and Huntington's disease.

The compounds of Formula I can be administered in one formulation or in separate formulations in combination with a neurotrophic factor or by themselves. The term "neurotrophic factor" relates to compounds that stimulate the growth and the proliferation of nerve cells. Numerous neurotrophic factors are known, such as, for example, NGF, BNDF, aFGF, bFGF, PDGF, BDNF, GDNF, CNTF, NT-3, NT-4/5 and IGF-1 and its derivatives such as gIGF-1 and Des(1-3)IGF-1. NGF is especially preferred for combined use.

For use of the compounds according to the invention as pharmaceutical agents, the latter are brought into the form of a pharmaceutical preparation, which in addition to the active ingredient contains vehicles, adjuvants and/or additives that are suitable for enteral or parenteral administration. The administration can be done orally or sublingually as a solid in the form of capsules or tablets or as a liquid in the form of solutions, suspensions, elixirs, aerosols or emulsions or rectally in the form of suppositories or in the form of injection solutions that optionally also can be administered subcutaneously, intramuscularly or intravenously, or topically or intrathecally. As adjuvants for the desired pharmaceutical agent formulation, the inert organic and inorganic carrier materials that are known to one skilled in the art are suitable, such as, e.g., water, gelatin, gum arabic, lactose, starch, magnesium stearate, talc, vegetable oils, polyalkylene glycols, etc. In addition, preservatives, stabilizers, wetting agents, emulsifiers or salts for changing the osmotic pressure or buffers can optionally be contained.

For parenteral administration, especially injection solutions or suspensions, especially aqueous solutions of active compounds in polyhydroxyethoxylated castor oil are suitable.

Topical administration is also defined as transdermal patches, ophthalmic preparations, aerosols for inhalation.

As carrier systems, surface-active adjuvants, such as salts of bile acids or animal or plant phospholipids, but also mixtures thereof as well as liposomes or components thereof can also be used.

For oral administration, especially tablets, coated tablets or capsules with talc and/or hydrocarbon vehicles or binders, such as, for example, lactose, corn or potato starch, are suitable. The administration can also be done in liquid form, such as, for example, as a juice, to which a sweetener is optionally added.

The dosage of the active ingredients can vary based on the method of administration, age and weight of the patient, type and severity of the disease that is to be treated and similar factors. The daily dose is 0.01–100 mg/kg of body weight/day, whereby the dose can be given as a single dose that is to be administered once or divided into two or more daily doses.

If combination therapy is performed, the dose can be reduced due to the synergistic action of the active ingredients. The neurotrophic factor is preferably administered in a dose of 0.01 µg–100 mg/kg/day together with the above-mentioned dose of the active ingredients.

The neurotrophic action of the compounds of Formula I and their physiologically compatible salts can be determined according to methods by W. E. Lyons et al., Proc. Natl. Acad. Sci. USA, 91, pages 3191–95 (1994).

The production of the compounds of Formula I is characterized in that in a compound of Formula II

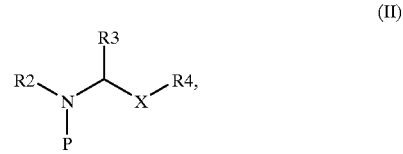

in which P is a protective group; X, $R^2$, $R^3$ and $R^4$ have the above-mentioned meaning, a) amino protective group P is cleaved off, b) Y—$R^1$ is introduced, and optionally the isomers are separated, and the salts are formed.

As protective group P, all known amino protective groups are suitable, such as alkoxycarbonyl groups, such as BOC, trimethylsilylalkoxycarbonyl groups, such as TeOC, i.a.

The cleavage of the amino protective group and the subsequent introduction of Y—$R^1$ is carried out according to known methods, which are described in, for example, U.S. Pat. No. 5,721,256 and WO 98/29117 and WO 98/13355.

The production of the compounds of Formula I can also be carried out in that a compound of Formula II, in which P is —CO—CO—O—$C_{1-6}$ alkyl, is reacted with organometallic compounds, such as, for example, Grignard compounds or lithium-organyls.

The optically active compounds of Formula I can be obtained with optically active starting materials or by separation according to commonly used methods, such as, for example, crystallization, chromatography or salt formation in the enantiomers or E/Z-isomers in the intermediate or final stages.

If the production of the starting compounds is not described, the latter are known or can be produced analogously to the processes that are known or according to the processes that are described here.

The production of the compounds of Formula II is carried out in that the NH-protected amino acid is converted with radical —X—$R^4$ into the desired heteroaryl derivative and acylated after the amino protective group is cleaved off.

To introduce the 1,2,4-oxadiazolyl radical, the protected amino acid can be reacted with amidoximes to

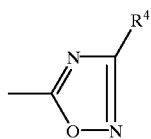

or the amidoxime of amino acid can be reacted with the corresponding anhydrides to

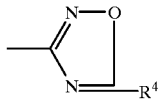

If the hydrazide of the amino acid is cyclized with ortho-carboxylic acid esters,

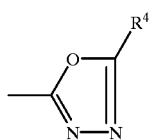

is obtained.

By reaction of the carbaldehydoxime with alkines,

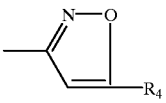

can be obtained.

If the amino acid thioamide is reacted with a-halogen ketones, compounds with —X—$R^4$ in the meaning of

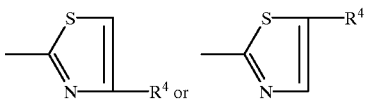

are obtained.

Oxazoles can be produced from, for example, carbaldehyde with isocyanides.

Below, the production of some precursors, intermediate products and products is described by way of example.

The presently disclosed compounds advantageously possess neuronal activity, without interfering with other pathways known to be affected by structurally similar compounds.

The nerve growth activity of the compounds of this invention may be initially assayed using several cell culture assays known in the art. For example, the compounds of this invention may be tested in neurite outgrowth assay using pheochromocytoma $PC_{12}$ cells as described by Lyons et al., PNAS, 91, pp. 3191–3195 (1994). A similar assay may be carried out in SH-SY5Y human neuroblastoma cells. Alternatively, the chick dorsal root ganglia assay described in U.S. Pat. No. 5,614,547 or in G. S. Hamilton et al., Bioorg. Med. Chem. Lett., (1997) and references cited therein, may be utilized.

The compounds of this invention may also be assayed for nerve growth activity in vivo using a mouse model of Parkinson's disease [J. P. Steiner et al., Proc. Natl. Acad. Sci. USA, 94, pp. 2019–23 (1997), U.S. Pat. No. 5,721,256] or following surgical sciatic nerve crush in rats.

These include, but are not limited to, trigeminal neuralgia, glossopharyngeal neuralgia, Bell's Palsy, myasthenia gravis, muscular dystrophy, muscle injury, progressive muscular atrophy, progressive bulbar inherited muscular trophy, herniated, ruptured or prolapsed invertebrae disk syndrome's, cervical spondylosis, plexus disorders, thoracic outlet destruction syndromes, peripheral neuropathies, such as those caused by lead, dapsone, ticks, or porphyria, other peripheral myelin disorders, Alzheimer's disease, Gullain-Barre syndrome, Parkinson's disease and other Parkinsonian disorders, ALS, multiple sclerosis, other central myelin disorders, stroke and ischemia associated with stroke, neural paropathy, other neural degenerative diseases, motor neuron diseases, sciatic crush, neuropathy associated with diabetes, spinal cord injuries, facial nerve crush and other trauma, chemotherapy- and other medication-induced neuropathies and Huntington's disease.

In another aspect, the method is used to stimulate nerve growth ex vivo. For this aspect, the compounds or compositions described above can be applied directly to the nerve cells in culture. This aspect of the invention is useful for ex vivo nerve regeneration.

According to an alternate embodiment, the method of stimulating neurite outgrowth or preventing neurodegeneration comprises the additional step of treating a patient or ex vivo nerve cells in culture with a neurotrophic factor, such as those contained in the compositions of this invention described above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding German application No. 199 05 256.5, filed Feb. 3, 1999, and U.S. Provisional Application No. 60/126,007 filed Mar. 24, 1999, are hereby incorporated by reference.

EXAMPLE 1 a) 3-(3-Pyridyl)-acrylonitrile 95 ml (0.60 mol) of cyanomethylphosphonic acid diethyl ester and 50 ml (0.55 mol) of pyridine-3-carbaldehyde are dissolved in 1 L of toluene and mixed with 55 g (0.55 mol) of $KHCO_3$. The mixture is heated for 1 hour in a preheated oil bath. The cooled mixture is mixed with additional toluene and washed with 1M $NaHCO_3$, twice with water and with saturated common salt solution. The organic phase is dried and concentrated by evaporation in a vacuum. The residue is recrystallized from ethyl acetate/hexane, and 49.5 g (69%) of product is obtained. Melting point 99.5–101° C.

$^{13}$C-NMR (75 MHz, CDCl): δ=98.8D (C-2); 117.4S (C-1); 123.9D (Py-5); 129.3S (Py-3); 133.5D (Py-4); 147.0D (Py-6); 149.0D (Py-2); 151.9D ppm (C-3).

b) 3-(3-Pyridyl)-propionamidoxime

Hydrogenation:

49.5 g (0.38 mol) of 3-(3-pyridyl)-acrylonitrile is dissolved in 428 ml of ethanol, 9.5 g of 10% Pd/C is added and hydrogenated under normal pressure. After the requisite hydrogen absorption, it is filtered off, and the filtrate is concentrated by evaporation in a vacuum. Chromatography ($CH_2Cl_2 \rightarrow CH_2Cl_2$/acetone 1:4) yields 38.3 g (76%) of 3-(3-pyridyl)propionitrile.

Reaction with hydroxylamine:

20.1 g (0.15 mol) of 3-(3-pyridyl)propionitrile is dissolved in a mixture of 61 ml of ethanol, and 15 ml of water and 9.5 g (0.14 mol) of hydroxylamine hydrochloride and 21 g (0.15 mol) of $K_2CO_3$ are added. After 24 hours at reflux, the solvent is removed in a vacuum, and the residue is extracted twice with ethanol. The extracts are concentrated by evaporation and recrystallized in hot ethanol. 14.1 g (56%) of product is obtained. Melting point 119–121° C.

c) 1,1-Dimethylethyl-(2S)-2-(3-(2-(3-pyridyl)ethyl)-1,2,4-oxadiazol-5-yl)-pyrrolidine-1-carboxylate 65.3 g (0.30 mol) of Boc-proline is dissolved in 822 ml of $CH_2C_{12}$ and mixed with 23.5 ml (0.15 mol) of diisopropyl-carbodiimide drop by drop at a temperature of 4–7° C. The is stirring is continued at 0° C. for 1 hour, the precipitate is filtered off, washed with $CH_2Cl_2$, and the combined filtrates are concentrated by evaporation in a vacuum. The anhydride is dissolved again in 822 ml of pyridine and mixed drop by drop with a solution of 25.1 g (0.15 mol) of 3-(3-pyridyl)-propionamidoxime in 276 ml of pyridine. Then, it is refluxed for 1 hour and allowed to stand overnight. The pyridine is distilled off in a vacuum, the residue is dissolved in dichloromethane and washed with saturated $NaHCO_3$ and water and dried.

Chromatography ($CH_2Cl_2$/acetone 98:2 1:1) yields 44 g (71) of product as an oil.

$^1$H-NMR (400 MHz, DMSO-$d_6$, 393K): δ=1.30 (s; 9H, Boc), 1.88–2.00 (m; 3H, 3-H, 4-$H_2$), 2.26–2.28 (m; 1H, 3-H), 3.02 (s; 4H, PyC$H_2$—C$H_2$), 3.40–3.49 (m; 2H, 5-$H_2$), 4.95–5.00 (m; 1H; 2-H), 7.20 (dd: 1H, Py-5), 7.57 (dt; 1H, Py-4), 8.25 (dd; 1H, Py-6), 8.41 ppm (d; 1H, Py-2) d) (2S)-3,3-Dimethyl-1-(-2-(3-(2-(3-pyridyl)ethyl)-1,2,4-oxadiazol-5-yl)-pyrrolidin-1-yl)-pentane-1,2-dione Cleavage of the Protective Group:

10.2 g (30 mmol) of 1,1-dimethylethyl-(2S)-2-(3-(2-(3-pyridyl)ethyl)-1,2,4-oxadiazol-5-yl)-pyrrolidine-1-carboxylate is dissolved in 270 ml of $CH_2Cl_2$ and mixed with 46 ml of trifluoroacetic acid at 0° C. The reaction mixture is brought to room temperature and stirred for 2 more hours. Water is added and set at pH 8 with $K_2CO_3$. The organic phase is washed with pH 7 buffer and saturated common salt solution and dried with $MgSO_4$. 5.20 g (72%) of unprotected compound.is obtained.

Acylation:

The compound that is obtained is dissolved in 50 ml of dichloromethane and cooled to 0° C. 5.9 ml (26 mmol) of triethylamine is added, and after 20 minutes, a solution of 2.85 ml (30 mmol) of methyloxalyl chloride in 34 ml of dichloromethane is added in drops. After 2 hours, dichloromethane is extracted. The organic phases are washed with saturated common salt solution and dried on $MgSO_4$. The solvent is drawn off, and 7.94 g of oil is obtained.

Grignard Reaction:

The product that is obtained above is dissolved in 141 ml of dry THF and cooled to −70° C. 31.6 ml (31.6 mmol) of a solution of 1,1-dimethylpropyl-magnesium chloride (1M in ether) is added in drops and stirred at this temperature for 2 more hours. The batch is allowed to stand overnight at room temperature. After saturated $NH_4Cl$ solution is added (while being cooled with ice), it is saturated with NaCl and extracted four times with ethyl acetate. The combined organic phases are washed with saturated common salt solution and dried on $MgSO_4$. The residue is chromatographed (hexane→hexane/acetone 6:4) to 6.15 g (55%) of clear oil.

$^{13}$C-NMR (75 MHz, $CDCl_3$): δ=8.9Q (8.8Q) (Val-5); 23.1Q (23.1Q) (Val-3-Me); 23.7Q (24.0Q) (Val-3-Me); 24.8T (21.8T) (C-3); 27.5T (27.4T) (C-4); 30.0T (Et-2); 30.4T (32.7T) (Et-1); 32.2T (32.8T) (Val-4); 47.0S (47.0S) (Val-3); 47.1T (46.4T) (C-5); 53.0D (54.0D) (C-2); 123.4D (Py-5); 135.5S (Py-3); 135.9D (Py-4); 147.9D (148.0D) (Py-6); 149.9D (Py-2); 165.1S (163.4S) (Val-1); 169.4S (169.5S) (Ox-3); 178.7S (179.0S) (Ox-5); 206.5S (206.0S) ppm (Val-2) (by-product in

EXAMPLE 2

3-(2-(3-Pyridyl)ethyl)-5-[(2S)-1-(3,4,5-trimethoxyphenylglyoxyloyl)-pyrrolidin-2-yl]1,2,4-oxadiazole 1. 2.45 g (7.13 mmol) of 5-[(2S)-1-(1,1-dimethylethoxycarbonyl)-pyrrolidin-2-yl]-3-(2-(3-pyridyl)-ethyl)-1,2,4-oxadiazole is dissolved in 114 ml of $CH_2Cl_2$, and 14 ml of trifluoroacetic acid is added at 0° C. After 2 hours at this temperature, the mixture is concentrated by evaporation in a vacuum, redissolved in $CH_2Cl_2$ and washed with 1M NaOH. The organic phase is dried on $Na_2SO_4$ and concentrated by evaporation in a vacuum. 1.52 g (87%) of crude product is obtained.

2. 6.51 g (27.1 mmol) of 3,4,5-trimethoxyphenylglyoxylic acid is dissolved in 40 ml of toluene, and 2.5 ml (27.6 mmol) of 1,1-dichloromethyl ether is added. The mixture is heated at 60° C. for 3 hours, cooled to room temperature and used in 3.

3. The amine that is obtained in 1. is dissolved in 22 ml of $CH_2C_{12}$, 4.2 ml (30 mmol) of triethylamine and the suspension that is obtained in 2 are added, and the mixture is stirred overnight at ambient temperature. The reaction is then diluted with $CH_2Cl_2$ and washed with saturated $NaHCO_3$ and brine and dried on $Na_2SO_4$. After the solvent has evaporated, 3.55 g of material is obtained, which is subjected to chromatography ($CH_2Cl_2 \rightarrow CH_2Cl_2$/EtOH 4:1) to give 1.77 g (53w) of the title compound as an oil.

$^{13}$C-NMR (75 MHz, $CDCl_3$): δ=24.7T (C 3), 27.6T (C 4) 30.0T (2$C_4$), 30.8T (2$C_3$), 47.2T (C 5), 53.4D (C 2), 56.4Q (1$C_8$), 61.1Q (1$C_9$), 107.3D (1$C_3$), 123.5D (2$C_8$), 127.5S (1$C_5$), 135.3S (2$C_6$), 135.9D (2$C_7$), 148.0D (2$C_9$), 149.9D (2$C_5$), 153.5S (1$C_4$), 165.4S (1C1), 169.6S (2$C_1$), 178.5S (2$C_2$), 189.7S ppm (1$C_2$).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of Formula I or a physiologically compatible salt thereof,

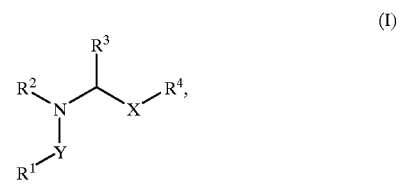

in which $R^1$ is hydrogen, Ar, straight-chain or branched $C_1$–$C_7$ alkyl, which can be substituted with Ar or E, straight-chain or branched $C_2$–$C_7$ alkenyl, which can be substituted with Ar or E, $C_3$–$C_7$ cycloalkyl, which can be substituted with Ar or E, or $C_5$–$C_7$ cycloalkenyl, which can be substituted with Ar or E, Y is —(C=O)—(C=O)—, —SO$_2$—, —(C=O)NH—, —(C=S)NH—, —(C=O)—(C=O)—O—, —(C=O)—(C=O)NH—, —(C=O)—O— or —SO$_2$—NH—, $R^2$ and $R^3$ together with the N-atom form pyrrnlidinyl, [a 5- to 7-membered heterocycle, which can be saturated or unsaturated and] which can be substituted with $C_1$–$C_4$ alkyl and OH, X is oxadiazolyl, $R^4$ is pyridinyl, straight-clhain or branched $C_1$–$C_9$ alkyl, straight-chain or branched $C_2$–$C_9$ alkenyl, $C_3$–$C_7$ cycloalkyl, or $C_5$–$C_7$ cycloalkenyl, wherein in each case the alkyl radical or the alkenyl radical is substituted with pyridinyl in one to two places, and Ar is a $C_6$–$C_{12}$ mono- or bicyclic aromatic compound, which optionally is partially hydrogenated and which can be substituted with E in one to three places, and E is halogen, hydroxy, nitro, $CF_3$, CN, $OCF_3$, amino, phenyl, methylenedioxy, phenoxy, benzyloxy, $C_1$–$C_4$ alkoxy or $C_1$–$C_4$ alkyl.

2. A compound according to claim 1, wherein $R^4$ means a straight-chain or branched $C_1$–$C_7$ alkyl radical, which is substituted with pyridinvl in one to two places.

3. A compound according to claim 1, in which $R^1$ means $C_1$–$C_7$ alkyl or Ar.

4. A compound of Formula IA, an isomer thereof or a physiologically compatible salt thereof

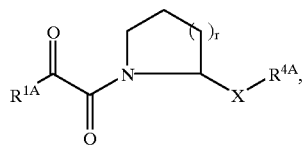

(IA)

in which, $R^{1A}$ is straight-chain or branched $C_1$–$C_7$ alkyl, straight-chain or branched $C_2$–$C_7$ alkenyl, $C_3$–$C_5$ cycloalkyl, $C_5$–$C_7$ cycloalkenyl or Ar' optionally substituted with halogen, hydroxy, nitro, $CF_3$, $C_1$–$C_4$ alkoxy or $C_1$–$C_4$ alkyl, X is oxadiazolyl, $R^{4A}$ is straight-chain or branched $C_1$–$C_7$ alkyl, straight-chain or branched $C_2$–$C_7$ alkenyl, $C_{3-5}$ cycloalkyl, or $C_5$–$C_7$ cycloalkenyl, wherein in each case the alkyl radical or the alkenyl radical is substituted with pyridinyl in one to two places, r is 1, and Ar' is $C_6$–$C_{12}$ aryl wherein the aryl radical is optionally substituted with halogen, hydroxy, $C_1$–$C_4$ alkoxy, nitro, $CF_3$ or $C_1$–$C_4$ alkyl by the same or a different component in one to three places.

5. A compound according to claim 1, wherein said compound is:

(2S)-3,3-Dimethyl-1-(-2-(3-(2-(3-pyridyl)ethyl)-1,2,4-oxadiazol-5-yl)-pyrrolidin-1-yl)-pentane-1,2-dione or a physiologically acceptable salt thereof; or 3-(2-(3-pyridyl)ethyl)-5-[(2S)-1-(3,4,5-trimethoxyphenylglyoxyloyl)-pyrrolidin-2-yl]1,2,4,-oxadiazole or a physiologically acceptable salt thereof.

6. A compound according to claim 1, wherein X is 1,2,4-oxadiazolyl.

7. A compound according to claim 1, wherein X is 1,3,4-oxadiazolyl.

8. A compound according to claim 1, Ar is 1-naphthyl, 2-naphthyl, biphenyl, indenyl, or phenyl.

9. A compound according to claim 1, wherein $R^1$ is Ar, straight-chain or branched $C_5$–$C_7$ allkyl which is optionally substituted with Ar or E, or $C_3$–$C_7$ cycloalkyl which is optionally substituted with Ar or E.

10. A compound according to claim 9, wherein $R^1$ is $C_3$–$C_7$ cycloalkyl which is substituted by E, and E is $C_1$–$C_4$ alkyl.

11. A compound according to claim 1, wherein $R^1$ is phenyl, phenyl substituted by E, straight-chain or branched $C_1$–$C_7$ alkyl, or straight-chain or branched $C_1$–$C_7$ alkyl substituted by E.

12. A compound according to claim 11, wherein $R^1$ is $C_{3-7}$ alkyl or 3,4,5-trimethoxy phenyl.

13. A compound according to claim 1, wherein Y is —SO$_2$—, —(C=O)NH—, —(C=S)NH—, —SO$_2$—N— or —(C=O)—(C=O)—.

14. A compound according to claim 1, wherein E is halogen, hydroxy, nitro, $CF_3$, CN, $C_1$–$C_4$ alkoxy or $C_1$–$C_4$ alkyl.

15. A compound according to claim 1, wherein $R^4$ is of the formula

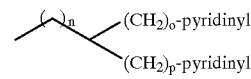

o and p arc each independently 0, 1, 2 or 3 and n is 0 or 1.

16. A compound of claim 1 which is 3-(2-(3-Pyridyl)ethyl)-5-[(2S)-1-(3,4,5-trimethoxyphenylglyoxyloyl)-pyrrolidin-2-yl]1,2,4-oxadiazole.

17. A pharmaceutical composition comprising an effective amount of a compound according to claim 1, and one or more pharmaceutically common vehicles and adjuvants.

18. A method for the treatment of Parkinson's disease in a patient, comprising administering to said patient an effective amount of a compound according to claim 1.

19. A method according to claim 18, wherein said compound is administered in a daily dose of 0.01–100 mg/kg of bodyweight.

20. A process for the production of a compound according to claim 1, comprising cleaving amino protective group P from a compound of Formula II

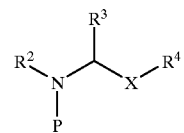

(II)

in which P is said amino protective group;

introducing Y—$R^1$; and optionally separating isomers; and optionally forming a salt.

* * * * *

UNITED STATES PATENT AND TRADEMARK OFFICE
CERTIFICATE OF CORRECTION

PATENT NO. : 6,284,779 B1
DATED : September 4, 2001
INVENTOR(S) : Thomas Brumby et al.

It is certified that error appears in the above-identified patent and that said Letters Patent is hereby corrected as shown below:

Column 13, claim 1,
Line 9, reads "pyrrnlidinyl" should read -- pyrrolidinyl --;
Line 9, delete "[a 5– to 7-membered heterocycle, which can be saturated or unsaturated and]"
Line 14, reads "straight-clhain" should read -- straight-chain --;

Column 14, claim 9,
Line 2, reads "$C_5$-$C_7$ allkyl" should read -- $C_1$-$C_7$ alkyl --;

Column 14, claim 15,
Line 3, reads "arc" should read -- are --.

Signed and Sealed this

Twelfth Day of March, 2002

*Attest:*

*Attesting Officer*

JAMES E. ROGAN
*Director of the United States Patent and Trademark Office*